US011219392B2

(12) United States Patent
Kainerstorfer et al.

(10) Patent No.: US 11,219,392 B2
(45) Date of Patent: Jan. 11, 2022

(54) VASCULAR OXIMETRY SYSTEM

(71) Applicant: Trustees of Tufts College, Medford, MA (US)

(72) Inventors: Jana M. Kainerstorfer, Pittsburgh, PA (US); Sergio Fantini, Winchester, MA (US); Angelo Sassaroli, Arlington, MA (US)

(73) Assignee: Trustees of Tufts College, Medford, MA (US)

( * ) Notice: Subject to any disclaimer, the term of this patent is extended or adjusted under 35 U.S.C. 154(b) by 1582 days.

(21) Appl. No.: 14/840,468

(22) Filed: Aug. 31, 2015

(65) Prior Publication Data

US 2017/0055893 A1 Mar. 2, 2017

(51) Int. Cl.
*A61B 5/1455* (2006.01)
*A61B 5/145* (2006.01)
*A61B 5/0205* (2006.01)
*A61B 5/021* (2006.01)
*A61B 5/08* (2006.01)
*A61B 5/00* (2006.01)

(52) U.S. Cl.
CPC ........ *A61B 5/14551* (2013.01); *A61B 5/0205* (2013.01); *A61B 5/14546* (2013.01); *A61B 5/021* (2013.01); *A61B 5/0816* (2013.01); *A61B 5/7203* (2013.01); *A61B 5/7225* (2013.01); *A61B 5/7253* (2013.01)

(58) Field of Classification Search
None
See application file for complete search history.

(56) References Cited

U.S. PATENT DOCUMENTS

| 6,216,021 | B1 |  | 4/2001 | Franceschini et al. |
| 6,430,513 | B1 | * | 8/2002 | Wang ................. A61B 5/14546 250/339.03 |
| 6,985,763 | B2 |  | 1/2006 | Fantini et al. |
| 2003/0133118 | A1 | * | 7/2003 | Braig ................. A61B 5/14532 356/432 |
| 2014/0219532 | A1 | * | 8/2014 | Pautot ................. A61B 5/0042 382/131 |
| 2015/0157271 | A1 | * | 6/2015 | Zhang ................. A61B 5/7246 600/324 |

FOREIGN PATENT DOCUMENTS

CA    2934869 A1 *  6/2014  ........... A61B 5/0075

OTHER PUBLICATIONS

Feng Zheng, Phasor representation of oxy- and deoxyhemoglobin concentrations: what is the meaning of out-of-phase oscillations as measured by near-infrared spectroscopy?, 2010, Journal of Biomedical Optics, vol. 15(4), pp. 1-3 (Year: 2010).*

* cited by examiner

*Primary Examiner* — Eric F Winakur
(74) *Attorney, Agent, or Firm* — Occhiuti & Rohlicek LLP

(57) ABSTRACT

A method for determining a hemoglobin saturation of a volume-oscillating vascular compartment in tissue includes receiving data representing measurements of a number of oscillating hemoglobin concentrations from the tissue and determining the hemoglobin saturation of the volume-oscillating vascular compartment to exclude an effect of an oscillating rate of supply of oxygenated blood to a portion of the tissue including removing a first contribution on one or more of the oscillating hemoglobin concentration measurements from at least one of the measurements, the first contribution being phase offset relative to said measurements.

19 Claims, 12 Drawing Sheets

VASCULAR OXIMETRY SYSTEM

BACKGROUND

This invention relates to optical oximetry systems.

Pulse oximetry is a technique that is based on the optical measurement of blood volume changes (photoplethysmography) to non-invasively measure an arterial oxygen saturation, $S^{(a)}$, in tissue. The basis of pulse oximetry is to measure an optical spectral signature of an arterial pulsatile signal at a cardiac frequency (i.e., a frequency at which a subject's heart beats). In some examples, two wavelengths of light, one in the red and one in the near-infrared region, are used for illuminating an extremity, such as a subject's fingertip, and measuring the transmitted light intensity.

When the subject's heart pumps blood, arteries expand in diameter and arterial blood volume increases. Such an increase in blood volume results in a greater hemoglobin concentration in tissue and a higher absorption of light, resulting in a reduction in the detected light from the tissue. Since oxygenated hemoglobin and deoxygenated hemoglobin have distinguishably different wavelength dependent absorption coefficients, a ratio of the pulsatile components of the measured intensities at the two wavelengths can be translated into hemoglobin saturation in the arteries. The pulsatile component of intensity at each wavelength is defined as the peak-to-peak change in intensity (due to cardiac pulsation) divided by the average intensity.

SUMMARY

In some examples, the blood circulation in biological tissues can be conceptually divided into different parts, each having different characteristics and functional roles: the collection of blood vessels that have a given characteristic and fulfill a given functional role in the tissue circulation is referred to as a "vascular compartment." Specifically, the "arterial compartment" transports blood under high pressure to the tissues, and have strong vascular walls. The "arteriolar compartment" comprises the smallest branches of the arterial system (arterioles are less than 100 microns in diameter), which feature muscular walls that can close or dilate the arterioles to control blood flow to the tissue. The "capillary compartment" consists of the smallest blood vessels (capillaries are less than 10 microns in diameter), which feature walls permeable to water and small molecules to exchange fluid, nutrients, electrolytes, and oxygen between blood and tissue. The "venular compartment" contains small vessels (venules are less than 300 microns in diameter) that collect blood from the capillaries and gradually coalesce into larger veins. The "venous compartment" consists of larger veins that transport blood back to the heart, and that have thin walls (because the blood pressure in the venous system is low) which can contract and expand to act as a controllable reservoir of blood.

In some examples, the hemoglobin saturation in the arterial compartment, $S^{(a)}$, is calculated from pulsatile intensities at two wavelengths by applying the modified Beer-Lambert law, which yields the pulsatile components of oxygenated and deoxygenated hemoglobin concentrations, $\Delta O(t)$ and $\Delta D(t)$, respectively. However, to translate the pulsatile intensity components at two wavelengths into the pulsatile components, $\Delta O(t)$ and $\Delta D(t)$, the differential path length factors at the two wavelengths need to be known. In the absence of this information, commercial pulse oximeters are typically based on an empirical calibration. This is typically done on healthy volunteers by calibrating optical measurements with actual $S^{(a)}$ values obtained on drawn arterial blood, in protocols that involve altering $S^{(a)}$ over a safe range by modulating the fraction of inspired oxygen ($FiO_2$). A key assumption in order to calculate the arterial saturation through the procedure described above is that the pulsatile intensity component originates only from the arterial blood volume. The error associated with finger pulse oximetry systems is typically reported to be about 4% and even greater for $S^{(a)} < 80\%$.

In some examples, the pulsatile intensity component includes both blood volume contributions originating from the arterial compartment and blood volume contributions originating from the venous compartment. Furthermore, it is known that capillary blood flow shows a pulsatile component that may also affect the measured optical signals. The hemoglobin saturation in blood changes while the blood flows through the smaller arterioles and capillary bed due to oxygen diffusion to the surrounding tissue. Consequently, a pulsatile capillary blood flow may influence the reading of $S^{(a)}$ by pulse oximetry, because of the flow-related change in the tissue concentrations of oxygenated and deoxygenated hemoglobin. Since the amplitude of the pulsatile blood volume changes are smaller in the brain than other tissues because of the rigid enclosure of the skull, it is to be expected that the influence of pulsatile capillary blood flow on $S^{(a)}$ measurements by pulse oximetry may be greater in the brain than other tissue locations such as the finger, toe, or ear lobe. As is described above, the underlying assumption to use pulsatile intensity changes for arterial saturation measurements is that the pulsatile intensity originates only from arterial blood. Any additional source of pulsatile intensity, be it from venous blood or pulsatile flow, invalidates the theory and negatively impacts the accuracy of arterial saturation measurements.

Using the same idea that forms the basis of pulse oximetry, (i.e., measuring the hemoglobin saturation of a specific vascular compartment by exploiting blood volume changes specific to that vascular compartment) near infra-red spectroscopy (NIRS) methods for measurements of venous saturation, $S^{(v)}$, have also been proposed. Microvascular $S^{(v)}$ measurements are especially important for cerebral monitoring, since they provide indications about oxygen extraction (the oxygen extraction fraction) and cerebral metabolic demand. Instead of using pulsations at the cardiac frequency, which predominantly impact the arterial blood volume, it has been proposed that respiration-induced blood pressure changes mostly affect the venous compartment because of the much larger vascular compliance in veins with respect to arteries. Therefore, it was proposed that oscillating hemoglobin concentration changes at the respiratory frequency may be used to measure the venous saturation. This method, sometimes called spiroximetry, has been validated in animal models and in human skeletal muscle, and applied to cerebral measurements in healthy subjects and ventilated patients. Measurements of oscillatory hemodynamics at the respiration rate are practically appealing for obtaining $S^{(v)}$ since they rely on spontaneous respiration and do not require one to apply any external maneuvers.

In addition to using oscillatory, respiration-induced hemodynamic changes, several methods for eliciting venous volume changes have been proposed. For example, one method for cerebral measurements is based on a head-down tilting protocol; tilting the head down by 15° results in venous pooling and hence a venous volume change. In this approach, the venous saturation is calculated from the difference in the cerebral concentrations of oxygenated and deoxygenated hemoglobin before and after head tilting.

Another example, for measurements on upper or lower extremities, involves eliciting venous volume changes by venous occlusion. Again, the difference in hemoglobin concentration before occlusion and during occlusion is used for estimation of $S^{(v)}$.

The pulse oximetry and spiroximetry techniques described above have been proposed to measure arterial and venous saturation, respectively, from optical measurements of time-varying vascular compartments. These techniques rely on an assumption that measured optical oscillations are dominated by blood volume changes, and that blood flow contributions are negligible. However, this assumption is not necessarily true for all types of tissues. Indeed, while blood volume oscillations are a major contributor to the optical signals at the respiration frequency, blood flow oscillations may also play a crucial role and need to be accounted for.

In some aspects, dynamic NIRS measurements of cerebral hemoglobin concentrations ($\Delta O(t)$ and $\Delta D(t)$) are translated into arterial and venous saturations, $S^{(a)}$ and $S^{(v)}$ without relying on the assumption that blood volume changes are the only source of the optical signal dynamics.

In a general aspect, a method quantifies the hemoglobin saturation of time-varying vascular compartments. Depending on the origin of the time variations, the method leads to absolute measurements of arterial saturation, venous saturation, or a combination of the two. In some examples, there are optical measurements of the temporal changes in the concentrations of oxygenated hemoglobin, $\Delta O(t)$, and deoxygenated hemoglobin, $\Delta D(t)$, as measured with near-infrared spectroscopy (NIRS) in the tissue of interest. These measurements of $\Delta O(t)$ and $\Delta D(t)$ are quantitatively analyzed using a hemodynamic model to correct for contributions from blood flow changes in the tissue, which were never taken into account before in this kind of measurement.

The method allows for separation of the contributions to $\Delta O(t)$ and $\Delta D(t)$ from pulsatile blood volume and pulsatile blood flow, which leads to more accurate estimations of cerebral $S^{(a)}$ and $S^{(v)}$ values. The method is based on using a hemodynamic model to identify the blood flow contributions to the measured hemoglobin concentration oscillations. From these flow contributions, one can determine the oscillatory blood volume contributions, which translate into the hemoglobin saturation of the volume-varying vascular compartment, be it arterial, venous, or a combination of both.

In some examples, in the case of oscillatory hemodynamics, such as those associated with the heart pulsation and respiration, the method uses a phasor representation to decompose the measured oscillations of the tissue concentrations of oxygenated hemoglobin (O) and deoxygenated hemoglobin (D) into their components associated with oscillatory blood volume (subscript V) and blood flow (subscript F): $O=O_V+O_F$, $D=D_V+D_F$. The hemoglobin saturation of the volume-oscillating vascular compartment, $$S_V = \frac{|O_V|}{|O_V|+|D_V|}$$

can be obtained after assuming the value of the phase angle between the measured oxygenated hemoglobin oscillations (O) and the flow oscillating component ($O_F$).

In another general aspect, a method for determining a hemoglobin saturation of a volume-oscillating vascular compartment in tissue includes receiving data representing measurements of a number of oscillating hemoglobin concentrations from the tissue. The hemoglobin saturation of the volume-oscillating vascular compartment is determined to exclude an effect of an oscillating rate of supply of oxygenated blood to a portion of the tissue including removing a first contribution on one or more of the oscillating hemoglobin concentration measurements from at least one of the measurements, the first contribution being phase offset relative to said measurements.

Aspects may include one or more of the following features.

The number of oscillating hemoglobin concentrations from the tissue may include a measured concentration of oxygenated hemoglobin, a measured concentration of deoxygenated hemoglobin, and a total hemoglobin concentration. The number of oscillating hemoglobin concentrations may oscillate at a frequency associated with a physiological function. The number of oscillating hemoglobin concentrations may oscillate at a cardiac frequency. The number of oscillating hemoglobin concentrations may oscillate at a respiratory frequency. The number of oscillating hemoglobin concentrations may oscillate at a physically induced frequency.

The effect of the oscillating rate of supply of oxygenated blood to the portion of the tissue may include an oscillation in the measured concentration of oxygenated hemoglobin and an oscillation in the measured concentration of deoxygenated hemoglobin due to oscillations in blood flow to the portion of the tissue. The oscillation in the measured concentration of oxygenated hemoglobin and the oscillation in the measured concentration of deoxygenated hemoglobin may be at least in part due to diffusion of oxygen from blood to the portion of the tissue.

The portion of the tissue may include a capillary compartment of the tissue. The volume-oscillating vascular compartment may include an arterial compartment. The volume-oscillating vascular compartment may include a venous compartment. The volume-oscillating vascular compartment may include a mixture of an arterial compartment and a venous compartment.

The method may include determining a first fraction of the hemoglobin saturation associated with the venous compartment and a second fraction of the hemoglobin saturation associated with the arterial compartment. The second fraction of the hemoglobin saturation may be determined based on a blood pressure measurement. The first fraction and the second fraction may be determined based on an empirically determined ratio.

Removing the first contribution on the one or more oscillating hemoglobin concentration measurements from the at least one measurement may include receiving an empirically derived representation of the phase offset. Removing the first contribution on the one or more oscillating hemoglobin concentration measurements from the at least one measurement may include receiving a representation of the phase offset, the representation being inferred using a coherent hemodynamics spectroscopy model.

In another general aspect, a system for determining a hemoglobin saturation of a volume-oscillating vascular compartment in tissue includes an input for receiving data representing measurements of a number of oscillating hemoglobin concentrations from the tissue and an oximetry processing module. The oximetry processing module determines the hemoglobin saturation of the volume-oscillating vascular compartment to exclude an effect of an oscillating rate of supply of oxygenated blood to a portion of the tissue including removing a first contribution on one or more of the oscillating hemoglobin concentration measurements from at least one of the measurements, the first contribution being phase offset relative to said measurements.

Aspects may include one or more of the following features.

The system may include a sensor for obtaining the data representing measurements of the number of hemoglobin concentrations from the tissue and providing the data to the input. The system may include an output for providing the determined hemoglobin saturation of the volume-oscillating vascular compartment. The system may include a display device for receiving a representation of the determined hemoglobin saturation of the volume-oscillating vascular compartment from the output and presenting the representation of the determined hemoglobin saturation of the volume-oscillating vascular compartment. The effect of the oscillating rate of supply of oxygenated blood to the portion of the tissue may include an oscillation in the measured concentration of oxygenated hemoglobin and an oscillation in the measured concentration of deoxygenated hemoglobin due to oscillations in blood flow to the portion of the tissue.

Removing the first contribution on the one or more oscillating hemoglobin concentration measurements from the at least one measurement may include receiving an empirically derived representation of the phase offset. Removing the first contribution on the one or more oscillating hemoglobin concentration measurements from the at least one measurement may include receiving a representation of the phase offset, the representation being inferred using a coherent hemodynamics spectroscopy model.

Aspects may have one or more of the following advantages.

The methods presented can be used to obtain accurate estimates of hemoglobin saturation in a volume varying compartment. In some examples, when the volume varying compartment is an arterial compartment, accurate estimates of arterial hemoglobin saturation can be obtained. In other examples, when the volume varying compartment is a venous compartment, accurate estimates of venous hemoglobin saturation can be obtained. In some examples, when both an arterial hemoglobin saturation and venous hemoglobin saturation of a tissue can be obtained, the oxygen extraction fraction of the tissue and hence a measure of the local tissue metabolic demand, can be obtained. Accurate measurement of any of the above quantities is clinically and diagnostically important.

In conventional pulse oximetry and spiroximetry approaches, an estimate of hemoglobin saturation in a volume varying compartment is obtained and then an assumption is made that the estimated hemoglobin saturation in the volume varying compartment corresponds to either an arterial hemoglobin saturation or a venous hemoglobin saturation. By using the approaches described herein to obtain a more accurate estimate of the hemoglobin saturation in the volume varying compartment, an accuracy of the results obtained by pulse oximetry and spiroximetry approaches can be improved.

Other features and advantages of the invention are apparent from the following description, and from the claims.

DESCRIPTION

1 Optical Oximetry Measurement System

Figure 1:
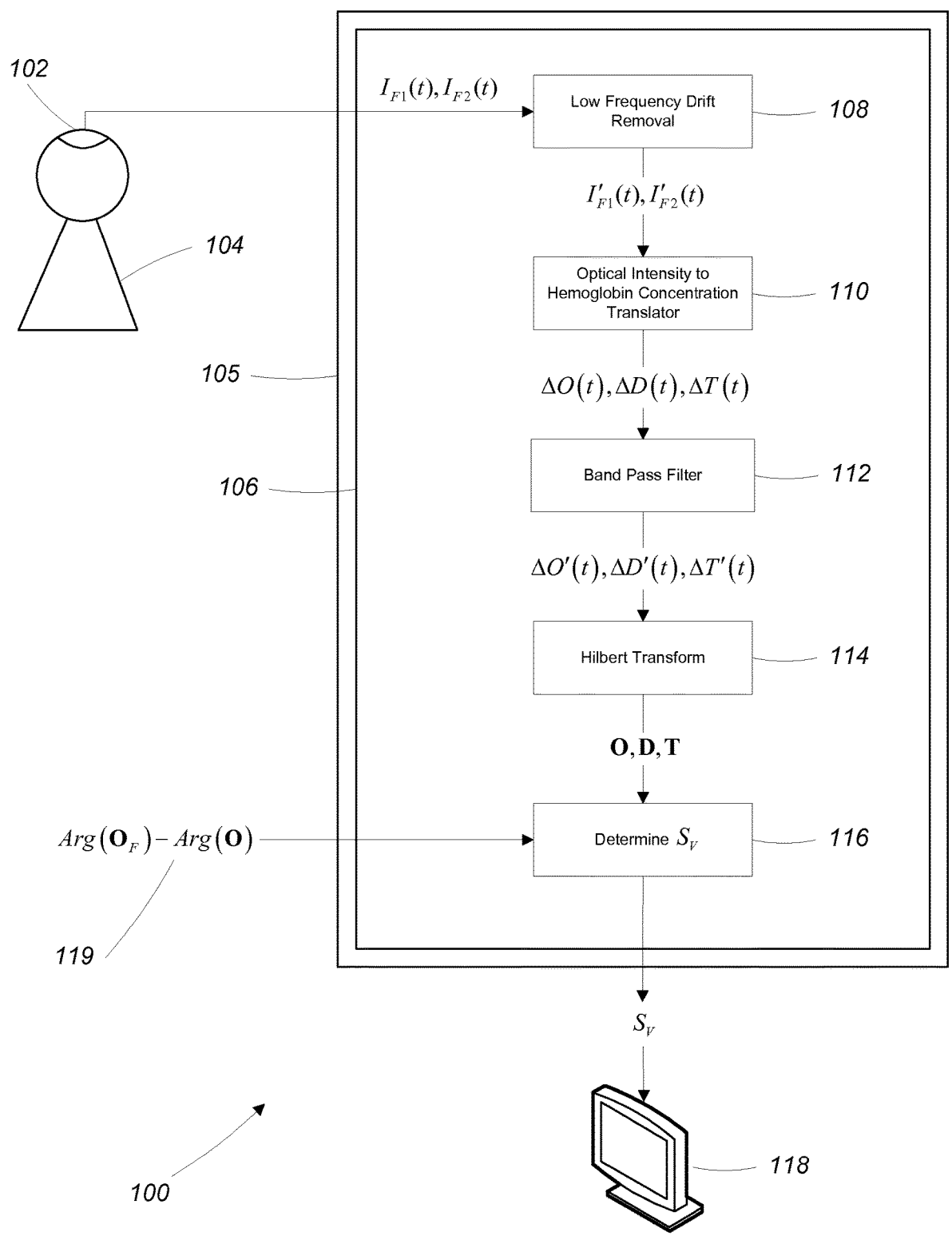
FIG. 1 is a schematic diagram of an oximetry system for determining the hemoglobin saturation of a volume-varying vascular compartment.

Referring to FIG. 1, an optical oximetry measurement system 100 includes an optical probe 102 secured to a body part of a subject 104, an oximetry processing module 106 implemented on a computing device 105, and a display device 118 (e.g., an LCD monitor). In some examples, the optical probe 102 is a probe of any near-infrared spectroscopy (NIRS) system, which operates at near-infrared wavelengths that are typically in the range of 650-900 nm. In some examples, the optical probe 102 is secured to the subject's head, in an area corresponding to the frontal lobe of the subject's brain and is secured in place by a dedicated cap.

The optical probe measures optical intensity data at two optical frequencies, $I_{F1}(t), I_{F2}(t)$ that reflect blood volume and/or blood flow oscillations occurring in a vascular compartment within the probed tissue volume. The optical intensity data $I_{F1}(t), I_{F2}(t)$ and assumed or inferred oximetry information 119 (described in greater detail below) are provided as input to the oximetry processing module 106 which processes the inputs to determine a hemoglobin saturation, $S_V$ of the volume oscillating vascular compartment of tissue. In some examples, the oximetry processing system 106 includes a low frequency drift removal module 108, optical intensity to hemoglobin concentration translator module 110, a band pass filter module 112, a Hilbert transform module 114, and a hemoglobin saturation calculation module 116.

In the oximetry processing system 106, the optical intensity data, $I_{F1}(t), I_{F2}(t)$ is first provided to the low frequency drift removal module 108 which removes slowly varying temporal drifts from the optical intensity data. The optical intensity data with any low frequency drift removed, $I'_{F1}(t), I'_{F2}(t)$ is provided to the optical intensity to hemoglobin concentration translator module 110 which translates changes in optical intensity into relative changes of the oxy-hemoglobin concentration in the oscillating vascular compartment, $\Delta O(t)$, the deoxygenated hemoglobin concentration in the oscillating vascular compartment, $\Delta D(t)$, and the total hemoglobin concentration in the oscillating vascular compartment, $\Delta T(t)$. In some examples, the optical intensity to hemoglobin concentration translator 110 performs the translation by applying the modified Beer-Lambert law to the optical intensity data.

The hemoglobin concentration signals output from the translator module 110, $\Delta O(t)$, $\Delta D(t)$, and $\Delta T(t)$ are passed to the band pass filter module 112 which band-pass filters the signals around a frequency of interest (e.g., a cardiac frequency in a range of 0.96-1.2 Hz or a respiratory frequency of approximately 0.1-0.3 Hz) using a linear-phase band-pass filter. In some examples, a greater filter width is chosen to accommodate possible changes in heart rate, respiratory rate, or other frequencies of interest over time.

The filtered hemoglobin concentration signals output from the band pass filter module 112, $\Delta O'(t)$, $\Delta D'(t)$, and $\Delta T'(t)$, are passed to the Hilbert transform module 114 which determines the instantaneous amplitudes and phases of the signals by applying the Hilbert transform to generate a complex analytic signal for each of the filtered hemoglobin concentration signals. The output of the Hilbert transform module 114 includes phasor representations of the filtered hemoglobin concentration signals, O, D, and T.

The phasor representations of the filtered hemoglobin concentration signals, O, D, T, and the assumed or inferred oximetry information 119 are provided to the hemoglobin saturation calculation module 116 which determines the hemoglobin saturation, $S_V$ of the volume oscillating vascular compartment.

1.1 Hemodynamic Model

In some examples, the hemoglobin saturation calculation module 116 utilizes a hemodynamic model to account for blood flow contributions to O and D when determining the hemoglobin saturation, $S_V$ of the volume oscillating compartment.

One example of such a hemodynamic model (described in U.S. patent application Ser. No. 14/654,133, which is incorporated by reference) describes time dependent expressions of the absolute tissue concentrations of O(t), D(t), and T(t) (with units of micromoles per liter of tissue) as a function of dynamic changes of cerebral blood volume (CBV) and cerebral blood flow (CBF) normalized to a baseline (cbv(t)= $\Delta CBV(t)/CBV_0$, cbf(t)=$\Delta CBF(t)/CBF_0$). The hemodynamic model also considers dynamic changes in the metabolic rate of oxygen, $cmro_2$. However, the dynamic changes in the metabolic rate of oxygen, $cmro_2$ are ignored in the oximetry measurement approaches described herein.

The model recognizes that the time evolution of hemoglobin concentrations in tissue depends on both the normalized dynamics of cerebral blood volume, cbv, and cerebral blood flow, cbf.

Figure 2:
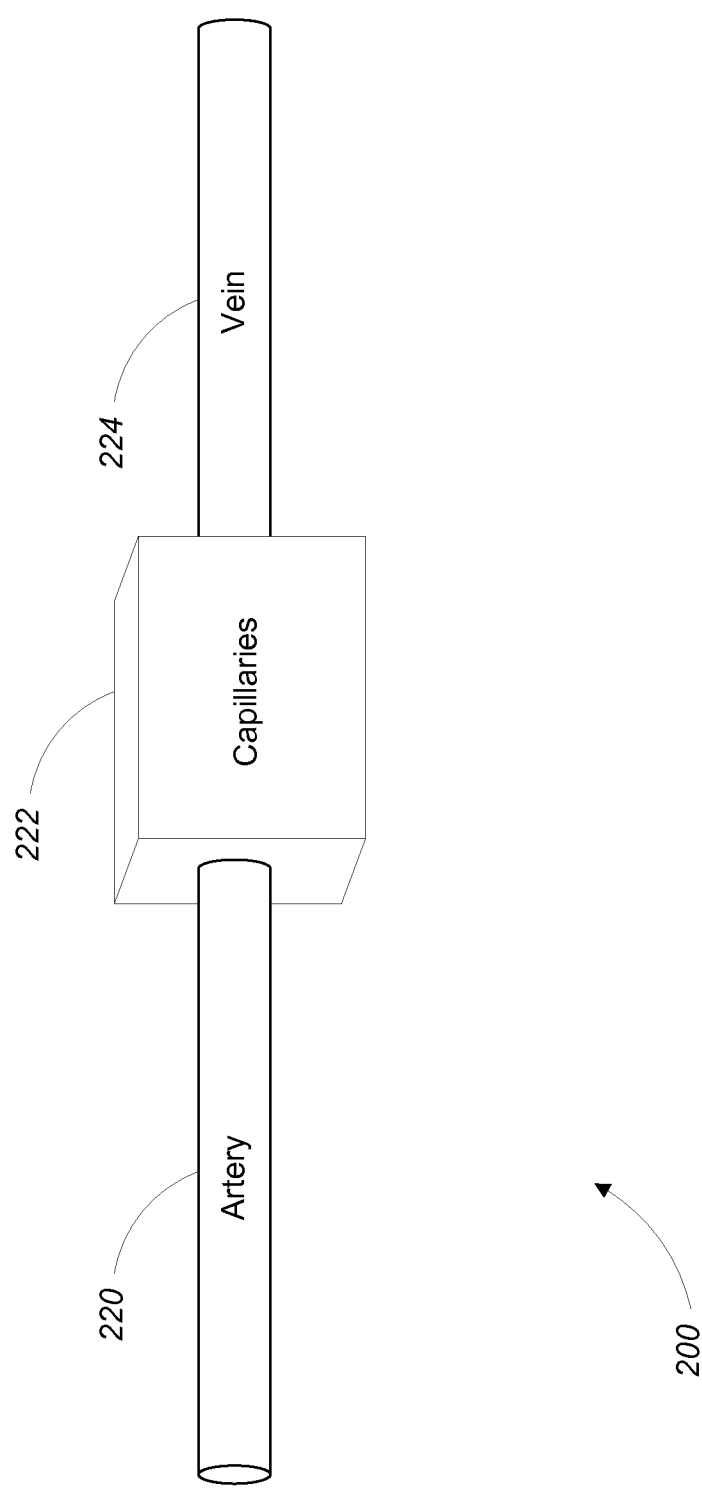
FIG. 2 is a vasculature model for tissue.

For example, referring to FIG. 2, an abstract representation of an oscillating vasculature in tissue 200 includes an arterial compartment 220, a capillary compartment 222, and a venous compartment 224. At the cardiac frequency, the oscillatory volume of blood in the arterial compartment 220, and in the venous compartment 224 (to some, usually negligible, extent) results in volume-driven oscillations in the concentrations of oxygenated hemoglobin and deoxygenated hemoglobin in the volume of tissue 200. The volume of blood in the capillary compartment 222 is substantially constant, but the blood flow through the capillaries oscillates at the cardiac frequency, resulting in flow-driven oscillations in the concentrations of oxygenated hemoglobin and deoxygenated hemoglobin in the volume of tissue 200.

Figure 3:
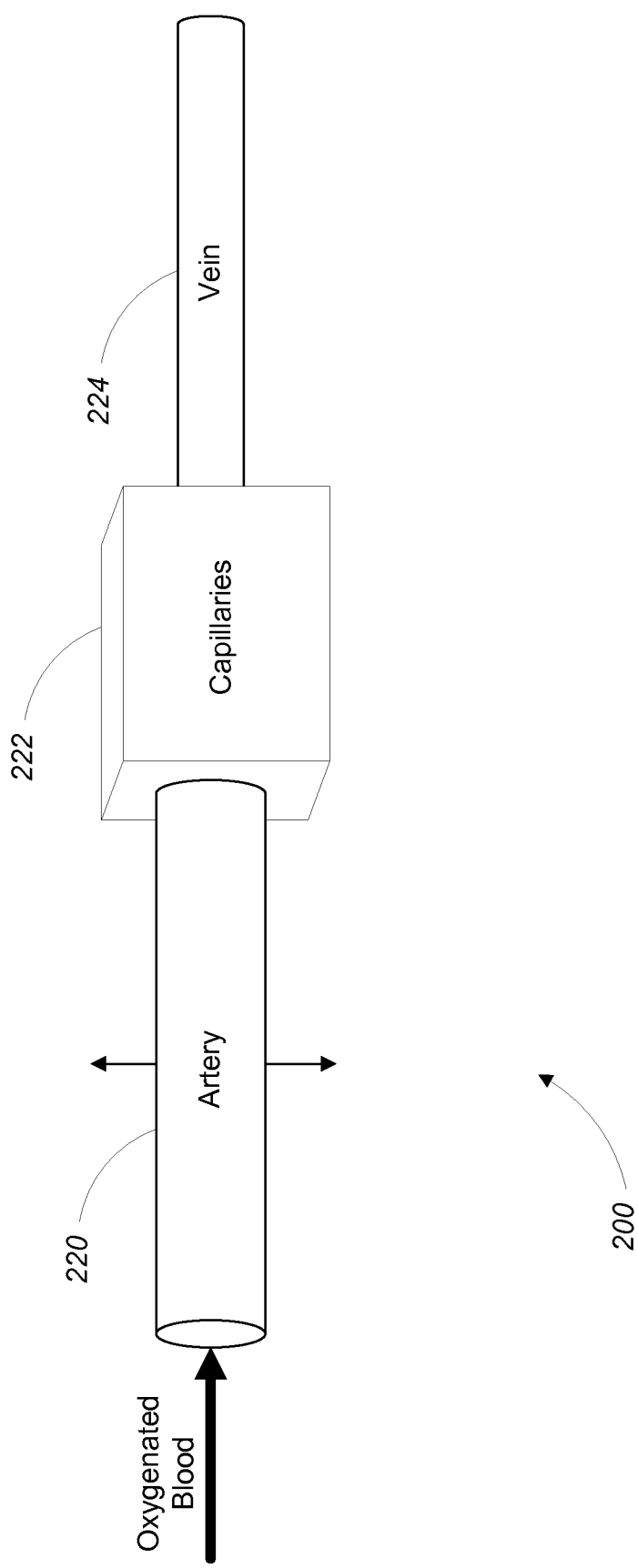
FIG. 3 shows a volume expansion of an arterial compartment of the vasculature model of FIG. 2.

For example, referring to FIG. 3, when a subject's heart beats, oxygenated blood enters the arterial compartment 220, causing the arteries to expand. For simplicity, it is assumed that expansion of the veins due to blood exiting the capillary compartment 222 and entering the venous compartment 224 is negligible. When the oxygenated blood in the arterial compartment 220 flows into the capillary compartment 222, the blood volume in the arterial compartment decreases and the arteries contract. This sequence of increasing and decreasing blood volume in the arterial compartment 220 causes volume-driven oscillations, at the cardiac frequency, of the concentrations of oxygenated hemoglobin and deoxygenated hemoglobin in the volume of tissue 200. In general, these volume-driven oscillations of the concentrations of oxygenated hemoglobin and deoxygenated hemoglobin are in phase with the volume oscillations of the arterial compartment 220.

Figure 4:
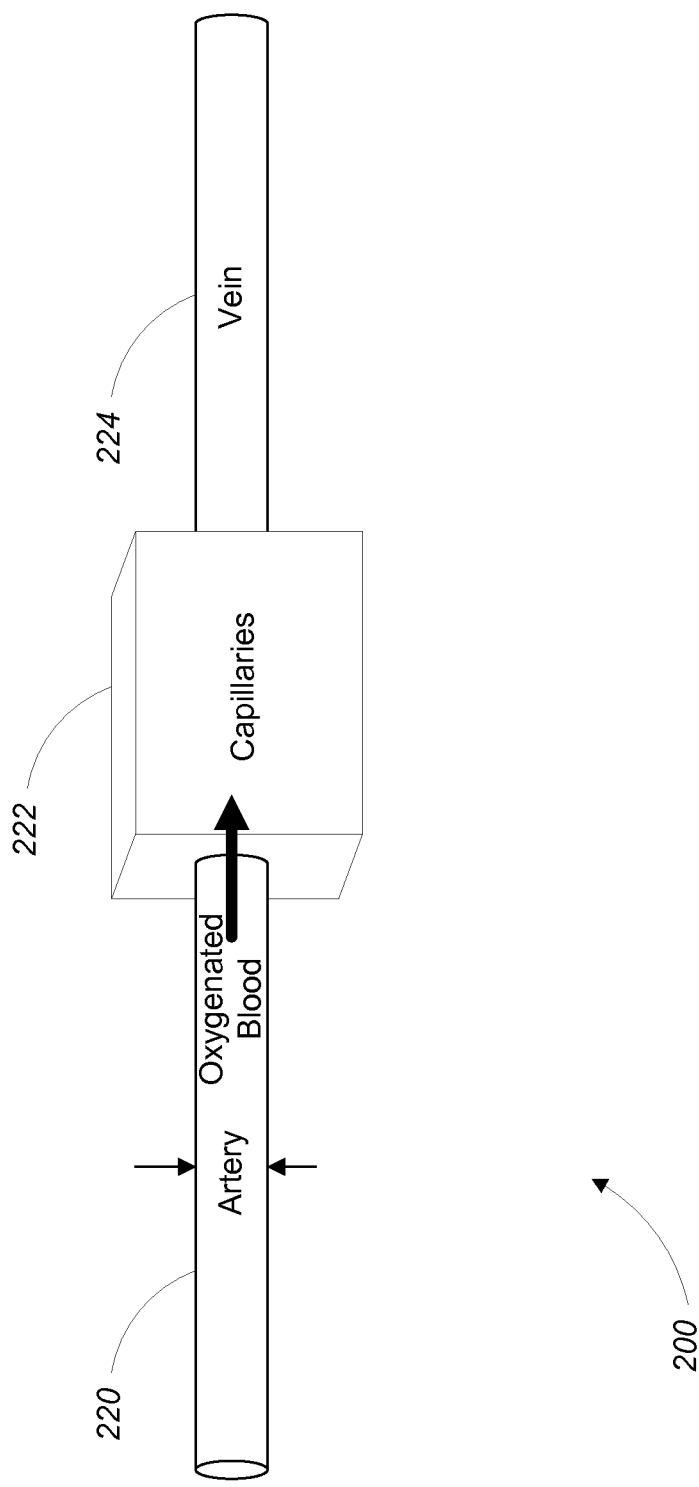
FIG. 4 shows blood flowing into a capillary compartment of the vasculature model of FIG. 2.

Referring to FIG. 4, as the oxygenated blood flows into the capillary compartment 222, the oxygenated hemoglobin concentration in the capillary compartment 222 increases and the deoxygenated hemoglobin concentration in the capillary compartment 222 decreases. As the blood flow into the capillary compartment 222 decreases, the oxygenated hemoglobin concentration in the capillary compartment 222 decreases and the deoxygenated hemoglobin concentration in the capillary compartment 222 increases. These fluctuations in the oxygenated and deoxygenated hemoglobin concentrations in the capillary compartment 222 due to oscillations in blood flow manifest as blood flow-driven oscillations, at the cardiac frequency, of oxygenated and deoxygenated hemoglobin in the volume of tissue 200. In general, blood flow-driven hemoglobin concentration oscillations are time delayed (i.e., phase lagged) with respect to the driving blood flow oscillations due to the time required for blood to flow through the capillary compartment 222.

Based on the above-described abstract representation of the hemodynamics of the volume of tissue 200, the quantities of absolute oxygenated hemoglobin concentration, O(t) and absolute deoxygenated hemoglobin concentration, D(t) in the volume of tissue 200 measurable by the optical probe 102 are written as a sum of blood flow $(O_F(t), D_F(t))$ and blood volume $(O_V(t), D_V(t))$ contributions, indicated with subscripts F and V, respectively. That is, in the hemodynamic model, the absolute oxygenated hemoglobin concentration, O(t) and the absolute deoxygenated hemoglobin concentration, D(t) in the volume of tissue 200 are defined as:

$$O(t) = O_V(t) + O_F(t)$$

$$D(t) = D_V(t) + D_F(t)$$

The hemodynamic model explicitly describes how time-dependent cerebral blood flow, cbf, and cerebral blood volume, cbv, yield the flow component of the absolute oxygenated hemoglobin concentration, $O_F(t)$, the volume component of the absolute oxygenated hemoglobin concentration, $O_V(t)$, the flow component of the absolute deoxygenated hemoglobin concentration, $D_F(t)$, and the volume component of the absolute deoxygenated hemoglobin concentration, $D_V(t)$. Relative changes of the oxygenated hemoglobin concentration in the oscillating vascular compartment, $\Delta O(t)$, the deoxygenated hemoglobin concentration in the oscillating vascular compartment, $\Delta D(t)$, can be determined by subtracting the baseline concentrations, $O_0(t)$ and $D_0(t)$, from O(t) and D(t), respectively.

Based on the above definitions of O(t) and D(t), the hemodynamic model can be used to describe the temporal dynamics of hemoglobin changes (expressed in the time domain), as well as sinusoidal hemodynamic oscillations as a function of the angular frequency, $\omega$ (expressed in the frequency domain). In the approaches described herein, the frequency domain version of the model for describing oscillating hemodynamic signals such as those related to cardiac pulsation and respiration is utilized. Sinusoidal oscillations in the relative changes of the oxygenated hemoglobin concentration, $\Delta O(t)$, the relative changes of the deoxygenated hemoglobin concentration, $\Delta D(t)$, and the relative changes of the total hemoglobin concentration, $\Delta T(t)$ in the volume of tissue 200 are represented as phasors: $O(\omega)$, $D(\omega)$, and $T(\omega)$. In the hemodynamic model, $O(\omega)$, $D(\omega)$, and $T(\omega)$ are expressed as a function of phasors that describe the oscillations of cerebral blood volume and blood flow ($cbv(\omega)$ and $cbf(\omega)$) as follows:

Oxygenated Hemoglobin Concentration $$O(\omega) = O_V(\omega) + O_F(\omega)$$

where $$O_V(\omega) = ctHb[S^{(a)}CBV_0^{(a)}cbv^{(a)}(\omega) + S^{(v)}CBV_0^{(v)}cbv^{(v)}(\omega)]$$

and $$O_F(\omega) = ctHb\left[\frac{\langle S^{(c)}\rangle}{S^{(v)}}(\langle S^{(c)}\rangle - S^{(v)})F^{(c)}CBV_0^{(c)}H_{LP}^{(c)}(\omega) + (S^{(a)} - S^{(v)})CBV_0^{(v)}H_{LP}^{(v)}(\omega)\right][cbf(\omega)]$$

Deoxygenated Hemoglobin Concentration $$D(\omega) = D_V(\omega) + D_F(\omega)$$

where $$D_V(\omega) = ctHb[(1 - S^{(a)})CBV_0^{(a)}cbv^{(a)}(\omega) + (1 - S^{(v)})CBV_0^{(v)}cbv^{(v)}(\omega)]$$

and $$D_F(\omega) = -ctHb\left[\frac{\langle S^{(c)}\rangle}{S^{(v)}}(\langle S^{(c)}\rangle - S^{(v)})F^{(c)}CBV_0^{(c)}H_{LP}^{(c)}(\omega) + (S^{(a)} - S^{(v)})CBV_0^{(v)}H_{LP}^{(v)}(\omega)\right][cbf(\omega)]$$

Total Hemoglobin Concentration $$T(\omega)=O_V(\omega)+D_V(\omega)=ctHb[CBV_0^{(a)}cbv^{(a)}(\omega)+CBV_0^{(v)}cbv^{(v)}(\omega)]$$

Note that the total hemoglobin concentration, $T(\omega)$ does not include contributions from flow components of the oxygenated or deoxygenated hemoglobin concentration, $O_F(\omega)$ and $D_F(\omega)$. The reason that $O_F(\omega)$ and $D_F(\omega)$ do not appear in $T(\omega)$ is that any flow change results in equal and opposite changes in the tissue concentrations of oxygenated hemoglobin and deoxygenated hemoglobin. In other words, it is generally true that $O_F(\omega)=-D_F(\omega)$ so that the flow-induced change in total hemoglobin concentration is zero (i.e., $O_F(\omega)+D_F(\omega)=0$)

In the above equations, $H_{LP}^{(c)}(\omega)$ is a complex transfer function associated with blood circulation in the capillary bed and is approximated by a resistor-capacitor (RC) low-pass filter which includes as a parameter the capillary transit time, $t^{(c)}$. $H_{LP}^{(v)}(\omega)$ is a complex transfer function associated with blood circulation in the venous compartment and is approximated by a time-shifted Gaussian low-pass filter, which includes as parameters the capillary transit time $t^{(c)}$ and the venous transit time $t^{(v)}$. ctHb is the hemoglobin concentration in blood. $F^{(c)}$ is the Fahraeus factor which represents a ratio of capillary-to-large vessel hematocrit. The superscripts (a),(c), and (v) for CBV, cbv, and hemoglobin saturation S indicate partial contributions from the arterial, capillary, and venous compartments, respectively. The total, steady state blood volume is given by $CBV_0=CBV_0^{(a)}+F^{(c)}CBV_0^{(c)}+CBV_0^{(v)}$. In the approaches described herein $cbv^{(c)}(\omega)=0$ due to the negligible dynamic dilation and recruitment of capillaries in the particular volume of tissue being measured (e.g., brain tissue).

Due to the high-pass nature of the cerebral autoregulation process that regulates cerebral blood flow in response to blood pressure changes, the following high-pass relationship between cbf and cbv is considered:

$$cbf(\omega) = kH_{HP}^{(AR)}(\omega)cbv(\omega) = kH_{HP}^{(AR)}(\omega)\left[\frac{CBV_0^{(a)}}{CBV_0}cbv^{(a)}(\omega) + \frac{CBV_0^{(v)}}{CBV_0}cbv^{(v)}(\omega)\right]$$

where k is the inverse of the modified Grubb's exponent, and $H_{HP}^{(AR)}(\omega)$ is an RC high-pass transfer function with cutoff frequency, $f_c^{(AR)}$, that describes the effect of autoregulation. Note that, in the following description, the above equations are only considered at a specific frequency (e.g., the cardiac frequency or the respiratory frequency) and the notation ($\omega$) is dropped, thus being implied.

1.2 Determining Hemoglobin Saturation with Negligible Blood Flow Oscillations

As was previously mentioned, for certain types of tissue, the dynamics of the tissue concentrations of oxygenated and deoxygenated hemoglobin are dominated by blood volume changes, with the effects of blood flow changes on the dynamics being negligible. In these types of tissues, the hemoglobin saturation of the volume oscillating compartment, $S_V$ (where the subscript V refers to a volume-oscillating compartment), can be calculated from the ratio of hemoglobin oscillation amplitudes as follows:

$$S_V = S^{(a)}\frac{|T^{(a)}|}{|T|} + S^{(v)}\frac{|T^{(v)}|}{|T|} = \frac{|O_V|}{|T|}$$

Note that subscript, V, is not used for the phasor T since the total hemoglobin concentration does not depend on the cerebral blood flow, cbf. Furthermore, since capillaries do not dilate, the capillary contribution to the volume oscillating hemoglobin saturation is negligible. Also note that it is assumed that the oscillations of arterial blood volume $cbv^{(a)}$ and the oscillations of venous blood volume $cbv^{(v)}$ are in phase with each other. Since the only volume oscillating compartments are the arterial and the venous compartments, the volume oscillating hemoglobin saturation falls within the values of the venous hemoglobin saturation, $S^{(v)}$ and the arterial hemoglobin saturation, $S^{(a)}$.

At the cardiac frequency (i.e., a heart rate of $\omega_{hr}/2\pi\approx 1$ Hz), oscillations in venous blood volume changes are negligible, so the oscillations of venous cerebral blood volume, $cbv^{(v)}=0$ and $S_V\approx S^{(a)}$. Furthermore, when it can be assumed that oscillating blood volume contributions to O and D are much greater than oscillating blood flow contributions (i.e., $|O_V|>>|O_F|$ and $|D_V|>>|D_F|$), the arterial hemoglobin saturation, $S^{(a)}$ can be calculated from the magnitudes of the O and D phasors as follows:

$$O_V^{(a)} = O_V = ctHb[S^{(a)}CBV_0^{(a)}cbv^{(a)}]$$

$$D_V^{(a)} = D_V = ctHb[(1 - S^{(a)})CBV_0^{(a)}cbv^{(a)}]$$

$$S^{(a)} = \frac{|O_T^{(a)}|}{|T|} = \frac{|O_V|}{|T|} = \frac{|O_V|}{|O_V + D_V|} = \frac{|O|}{|T|} = \frac{|O|}{|O|+|D|}$$

In this case, since oscillations in blood flow are negligible and blood volume changes are the only source of contributions to O and D, oscillations in oxygenated and deoxygenated hemoglobin are in phase (i.e., Arg(D)–Arg(O)=0).

Figure 5:
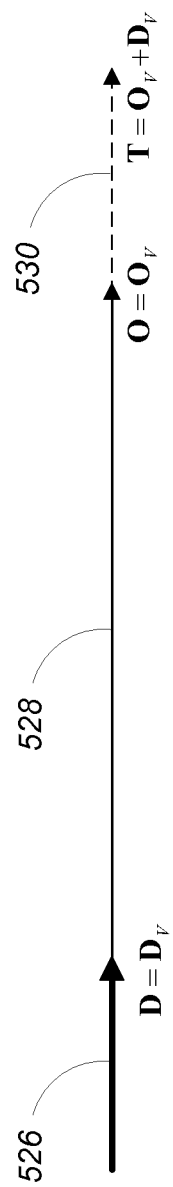
FIG. 5 is a phasor diagram for determining a hemoglobin saturation of a volume of tissue with negligible blood flow oscillations.

Referring to FIG. 5, a phasor diagram includes a first arrow 526 representing the oscillating deoxygenated hemoglobin concentration phasor, D, a second arrow 528 representing the oscillating oxygenated hemoglobin concentration phasor, O, and a third arrow 530 representing the oscillating total hemoglobin concentration, T.

In the scenario depicted in FIG. 5, since the oscillating blood flow contributions, $O_F$ and $D_F$ are negligible and O and D are in phase, the arterial hemoglobin saturation, $S^{(a)}$ is determined by the hemoglobin saturation calculation module 116 of FIG. 1 as a ratio of a magnitude of the oscillating oxygenated hemoglobin concentration phasor, O to a magnitude of the oscillating total hemoglobin concentration phasor, T as follows:

$$S^{(a)} = \frac{|O|}{|T|} = \frac{|O_V|}{|T|}$$

1.3 Determining Hemoglobin Saturation with Non-Negligible Blood Flow Oscillations For certain types of tissues (e.g., brain tissue) the dynamics of the tissue concentrations of oxygenated and deoxygenated hemoglobin are affected by both blood volume changes and blood flow changes (i.e., the effects of blood flow changes on the dynamics are not negligible). In such cases, to achieve an accurate measurement of the hemoglobin saturation for a volume oscillating vasculature, $S_V$, the oscillating blood flow contribution, $O_F$ to the oxygenated hemoglobin concentration O, the oscillating blood flow contribution, $D_F$ to the deoxygenated hemoglobin concentration, D, and hence the cerebral blood flow, cbf, terms in the model equations described above are taken into account.

In general, the effects of cerebral blood flow, cbf introduce a frequency dependent phase shift between the measured oxygenated hemoglobin concentration, and deoxygenated hemoglobin concentration. That is, the phase difference, Arg(D)–Arg(O), between the phasor representing the oscillating oxygenated hemoglobin concentration, O and the phasor representing the oscillating deoxygenated hemoglobin concentration, D is not equal to 0°. Due to this phase difference, the magnitude of the measured oscillating oxygenated hemoglobin concentration is not simply equal to the magnitude of the oscillating blood volume component of the measured oscillating oxygenated hemoglobin concentration (i.e., $|O| \neq |O_V|$) but instead must account for the oscillating blood flow component ($O_F$). Thus, the model equation for the oscillating oxygenated hemoglobin concentration at the cardiac frequency, hr, taking oscillating blood flow into account is:

$$O(hr) = ctHb[S^{(a)}CBV_0^{(a)}cbv^{(a)}(hr)] + ctHb\left[\frac{\langle S^{(c)} \rangle}{S^{(v)}}(\langle S^{(c)} \rangle - S^{(v)})F^{(c)}CBV_0^{(c)}H_{LP}^{(c)}(hr) + (S^{(a)} - S^{(v)})CBV_0^{(v)}H_{LP}^{(v)}(hr)\right][cbf(hr)]$$

and the model equation for the oscillating deoxygenated hemoglobin concentration at the cardiac frequency, hr, taking oscillating blood flow into account is:

$$D(hr) = ctHb[(1 - S^{(a)})CBV_0^{(a)}cbv^{(a)}(hr)] - ctHb\left[\frac{\langle S^{(c)} \rangle}{S^{(v)}}(\langle S^{(c)} \rangle - S^{(v)})F^{(c)}CBV_0^{(c)}H_{LP}^{(c)}(hr) + (S^{(a)} - S^{(v)})CBV_0^{(v)}H_{LP}^{(v)}(hr)\right][cbf(hr)]$$

The hemoglobin saturation for the volume oscillating vasculature in tissue, taking oscillating blood flow into account is:

$$S_V = \frac{|O_V|}{|T|} \neq \frac{|O|}{|T|}$$

Furthermore, since the O and D phasors are not in phase, $$\frac{|O|}{|O|+|D|} \neq \frac{|O|}{|O+D|}$$

1.3.1 Phasor Based Approach

Figure 6:
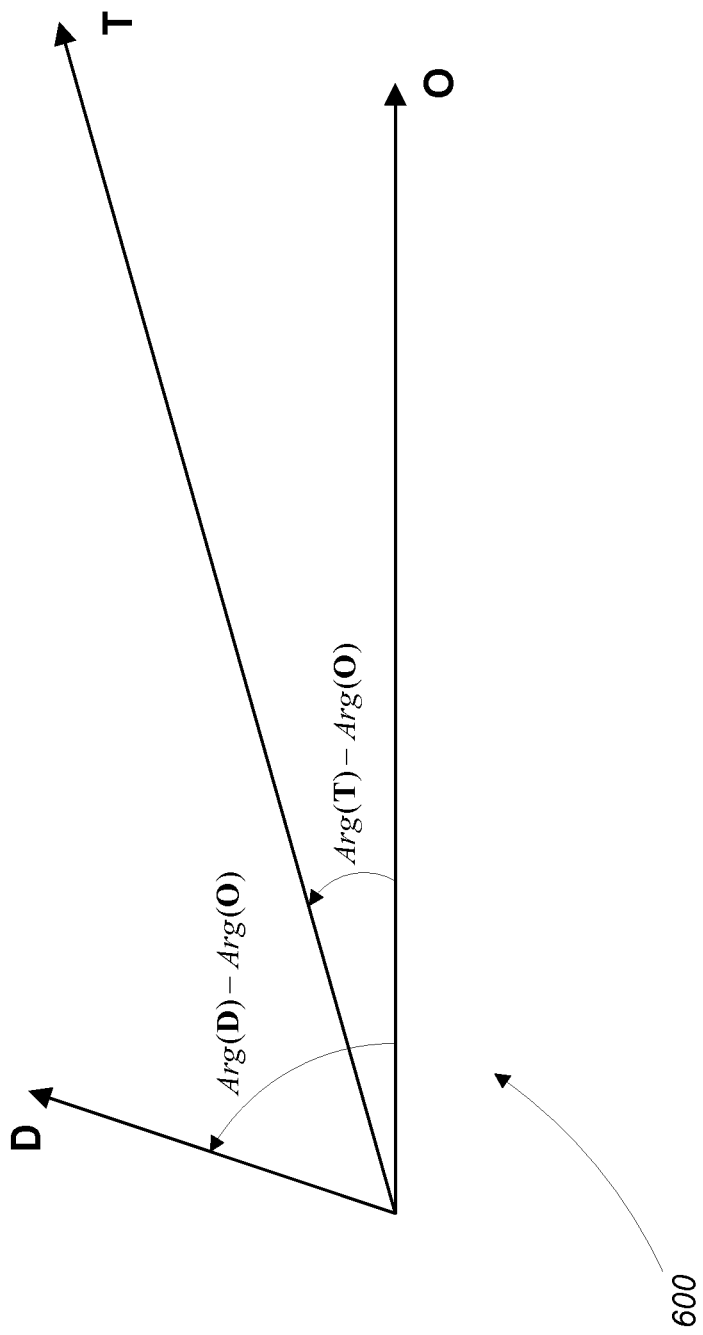
FIG. 6 is a phasor diagram illustrating measured hemodynamic quantities for a volume of tissue with non-negligible blood flow oscillations.

Referring to FIG. 6, based on the above information, the hemoglobin saturation for a volume oscillating vascular compartment in tissue, $S_V$, is determined by the hemoglobin saturation calculation module 116 of FIG. 1 by first measuring O, D, and T. From the measured O, D, and T, the phase angle between D and O (i.e., Arg(D)–Arg(O)) and the phase angle between T and O (i.e., Arg(T)–Arg(O)) can be determined. With O, D, T, Arg(D)–Arg(O), and Arg(T)–Arg(O) known, the phasor diagram 600 of FIG. 6 can be constructed.

As is noted above, $T=O_V+D_V$, where $O_V$ and $D_V$ are in phase. Thus, the $O_V$ and $D_V$ phasors extend in a direction along the T phasor. Note, however that the magnitudes of $O_V$ and $D_V$ are yet to be determined.

Figure 7:
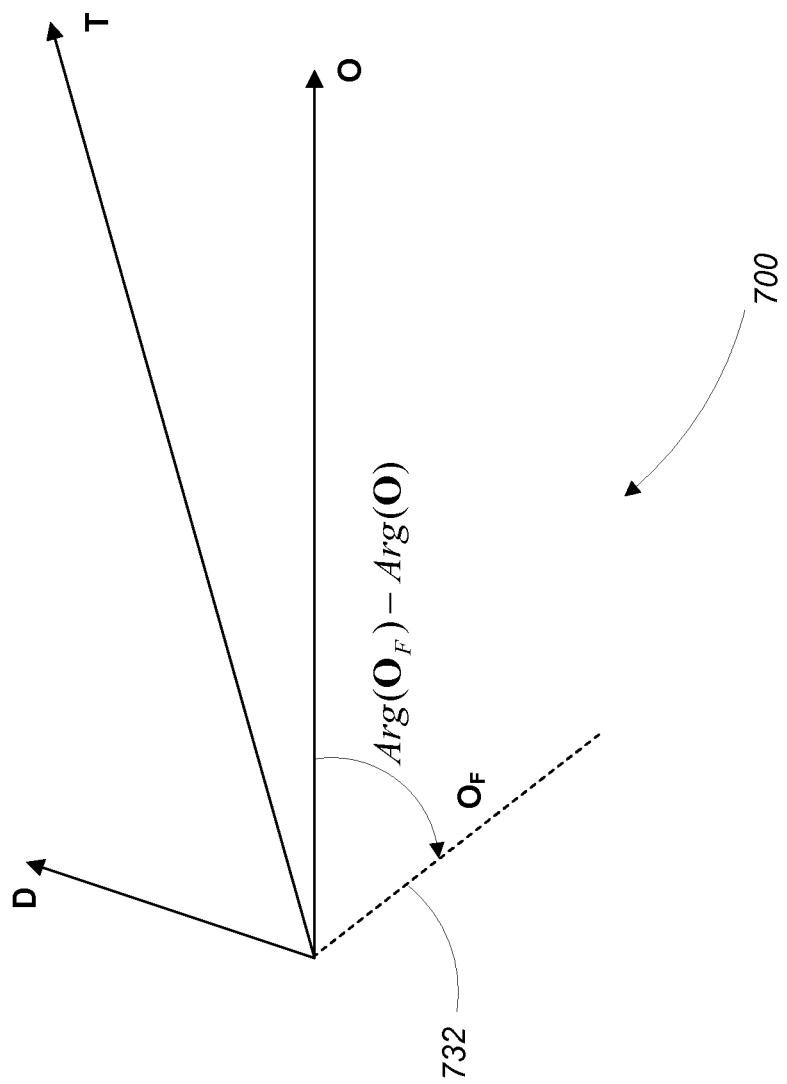
FIG. 7 is the phasor diagram of FIG. 6 including an assumed angle between a blood flow contribution to the oxygenated hemoglobin concentration in the tissue, $O_F$ and the oxygenated hemoglobin concentration in the tissue, O.

Referring to FIG. 7, to determine the magnitude of $O_V$, a value for the phase angle between $O_F$ and O, Arg($O_F$)–Arg(O) is assumed or inferred using the hemodynamic model. That is, Arg($O_F$)–Arg(O) is the assumed or inferred value corresponding to element 119 of FIG. 1.

A first line 732 is drawn on the phasor diagram 700 extending from the origin at the angle Arg($O_F$)–Arg(O). Note that, in the phasor diagram 700 of FIG. 7, the phase angle of $O_F$ is assumed to be known, but the magnitude of $O_F$ is unknown.

Figure 8:
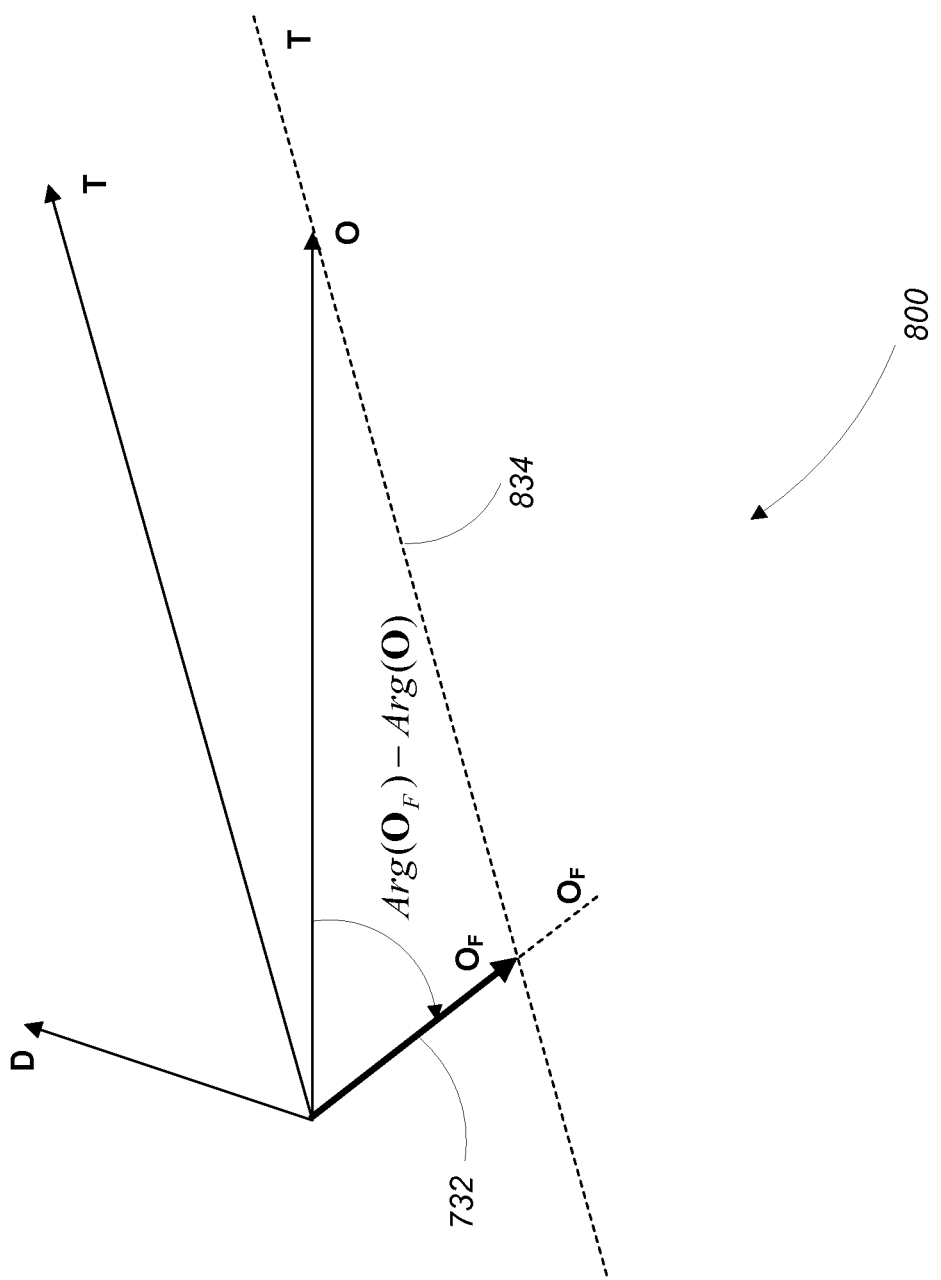
FIG. 8 is the phasor diagram of FIG. 7 with a magnitude of the blood flow contribution to the oxygenated hemoglobin concentration in the tissue, $O_F$ determined.

Referring to FIG. 8, knowing that $O_V$ is in phase with T, the magnitude of $O_F$ is determined by drawing a second line 834 in the phasor diagram 800 parallel to the T phasor and intersecting with the tip of the O phasor. The point of intersection of the second line 834 with the first line 732 is the tip of $O_F$. With the tip of $O_F$ identified, both the magnitude and phase of $O_F$ are determined.

Figure 9:
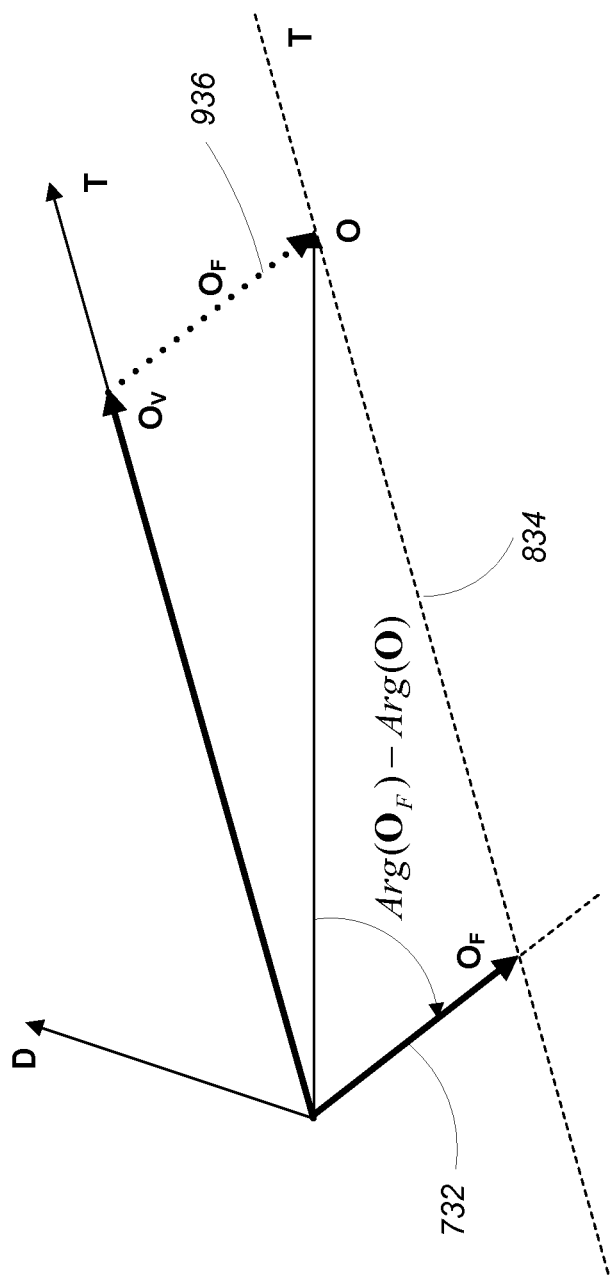
FIG. 9 is the phasor diagram of FIG. 8 with a magnitude of a blood volume contribution to the oxygenated hemoglobin concentration in the tissue, $O_V$ determined.

Referring to FIG. 9, with both the magnitude and phase of $O_F$ determined, $O_V$ is determined by drawing a third line 936 parallel to $O_F$ and intersecting with the tip of the O phasor. The point of intersection of the third line 936 with the T phasor is the tip of the $O_V$ phasor. With the tip of $O_V$ identified, both the magnitude and phase of $O_V$ are determined.

With $O_V$ and T known, the hemoglobin saturation calculation module 116 of FIG. 1 determines the hemoglobin saturation $S_V$ as:

$$S_V = \frac{|O_V|}{|T|}$$

Note that, at the cardiac frequency, the venous contribution to the hemoglobin saturation, $S_V$ is negligible, so the hemoglobin saturation $S_V$ is considered to be approximately equal to the arterial hemoglobin saturation, $S^{(a)}$.

Figure 10:
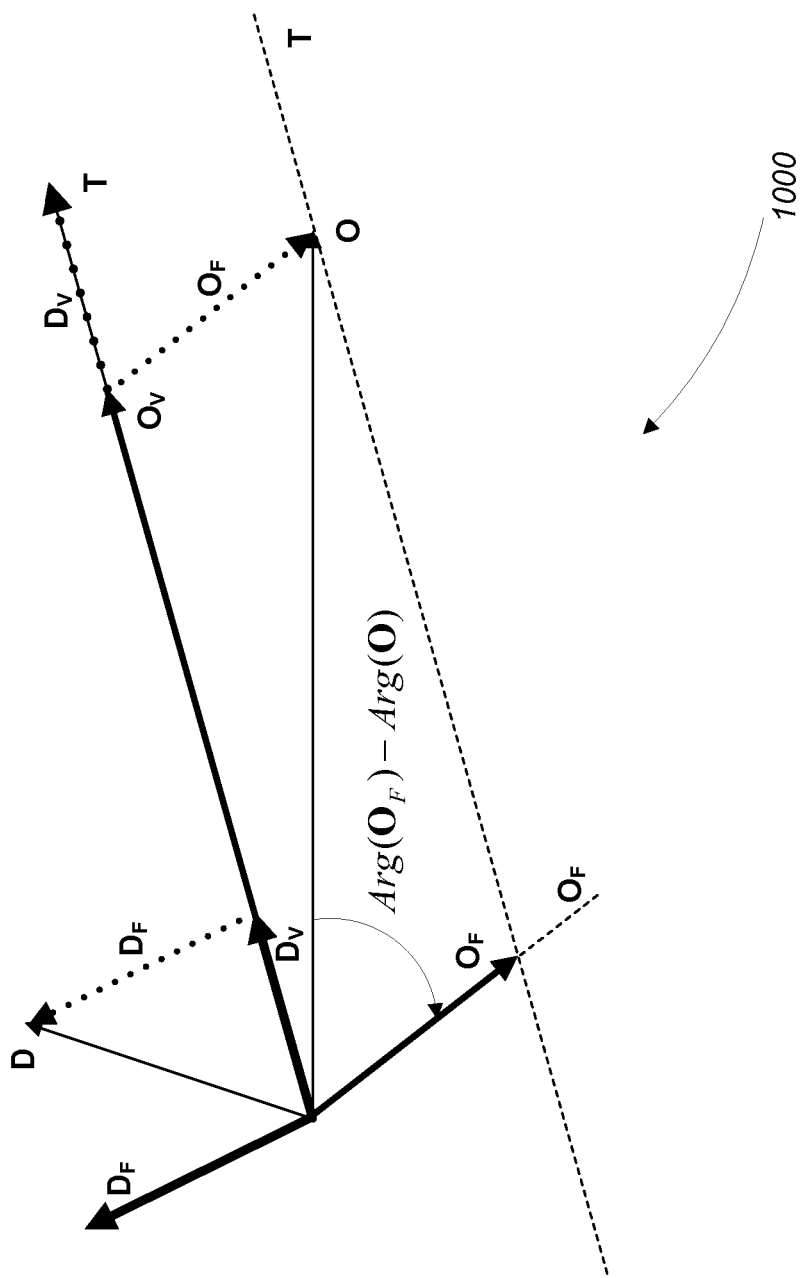
FIG. 10 illustrates the solution to the phasor diagram of FIG. 9.

Referring to FIG. 10, with $O_V$ and $O_F$ determined, the phasor diagram 1000 can be fully solved using phasor algebra to determine $D_V$ and $D_F$.

1.3.2 Algebraic Phasor Diagram Analysis Approach

Figure 11:
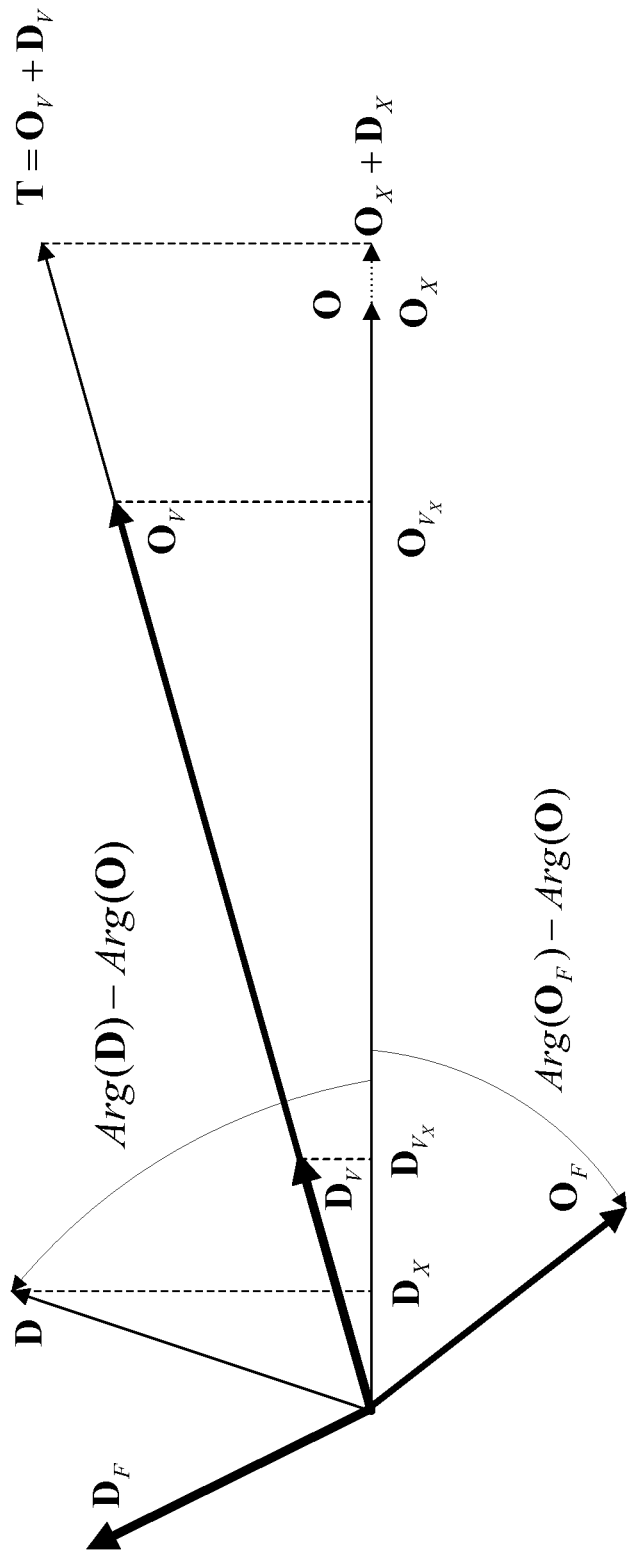
FIG. 11 is an alternative representation of the phasor diagram of FIG. 10.

Referring to FIG. 11, in some examples an algebraic analysis of the phasor diagram for O, D, and T yields the following set of equations:

$O_{Vx} = S_V(O_x + D_x)$ $O_{Vy} = S_V(D_y)$ $O_{Fx} = (1 - S_V)O_x - (S_V)D_x$ $O_{Fy} = -(S_V)D_y$ $D_{Vx} = (1 - S_V)(O_x + D_x)$ $D_{Vy} = (1 - S_V)(D_y)$ $D_{Fx} = -[(1 - S_V)O_x - (S_V)D_x]$ $D_{Fy} = (S_V)D_y$ where the subscripts x and y indicate the x and y components, respectively, of corresponding phasors. There are 8 equations in the set of equations and there are 9 unknowns (i.e., the two components of the phasors $O_V$, $D_V$, $O_F$ and $D_F$, and $S_V$). If $S_V \approx S^{(a)}$ is known or assumed, $O_V$, $D_V$, $O_F$ and $D_F$ can be determined using the above equations. Alternatively, one may assume another quantity (e.g., the angle between $O_F$ and O) and then solve the set of equations to determine the value of $S_V$.

1.4 Determining Hemoglobin Saturation of Volume Oscillating Vascular Compartments with Non-Negligible Blood Flow Oscillations In the examples above, oscillations at the cardiac frequency are leveraged to measure hemoglobin saturation in a volume oscillating vasculature in tissue, $S_V$. Since oscillations in the venous compartment at the cardiac frequency are generally considered to be negligible, $S_V$ at the cardiac frequency. However, in some examples, the hemoglobin saturation of volume oscillating vascular compartments may be representative of the venous hemoglobin saturation, $S^{(v)}$ (a desirable measure, for example, to assess the local tissue oxygen consumption). In particular, at the respiration frequency, venous blood volume oscillations are the dominant source of oxygenated and deoxygenated hemoglobin concentration dynamics. Using venous blood volume oscillations at the respiration frequency to calculate $S^{(v)}$ is referred to as spiroximetry.

As was the case in previous examples, since blood flow contributions are not negligible for brain measurements, $S_V$ can not be determined as:

$$\frac{|O|}{|O+D|}$$

from data collected during paced or normal breathing, or from data reflecting other kinds of spontaneous or induced hemodynamic oscillations. Thus, to determine $S_V$, a value for the phase difference between the flow component of the oxygenated hemoglobin concentration phasor ($O_F$) and the measured oxygenated hemoglobin concentration phasor (O) is assumed. In some examples, the value for the relative phase $(\text{Arg}(O_F) - \text{Arg}(O))$ is estimated by using the hemodynamic model. Based on the assumed or inferred relative phase, and after considering that $\text{Arg}(O_V) = \text{Arg}(T)$, $S_V$ is determined in the manner as above with the equations for the algebraic phasor diagram analysis approach, resulting in the expression:

$$S_V = \frac{O_x \tan(\text{Arg}(O_F) - \text{Arg}(O))}{(O_x + D_x)\tan(\text{Arg}(O_F) - \text{Arg}(O)) - D_y}$$

Alternatively, $S_V$ can also be determined by the hemoglobin saturation calculation module 116 of FIG. 1 using the phasor based approach described above.

Note that the hemodynamic model can identify a range of physiological values for the relative angle, $\text{Arg}(O_F) - \text{Arg}(O)$, from which $S_V$, the saturation of the volume oscillating compartments, can be determined. When arterial volume oscillation at the respiration frequency cannot be considered to be negligible, the oscillating total hemoglobin concentration has both arterial and venous contributions (i.e., $T = T^{(a)} + T^{(v)}$). It is assumed that the arterial and venous volume oscillations are in phase with each other (i.e., $\text{Arg}(T^{(a)}) - \text{Arg}(T^{(v)}) = 0°$ and $|T| = |T^{(a)}| + |T^{(v)}| = |T^{(a)} + T^{(v)}|$. Therefore, a factor, $\rho^{(v)}$ is introduced (where $0 \leq \rho^{(v)} \leq 1$), the factor specifying the venous fraction of the total oscillating blood volume. In other words, $$\rho^{(v)} = \frac{|T^{(v)}|}{|T^{(a)}| + |T^{(v)}|}$$

and $$1 - \rho^{(v)} = \frac{|T^{(a)}|}{|T^{(a)}| + |T^{(v)}|}.$$

Thus, the hemoglobin saturation of the volume oscillating compartment can be written as:

$$S_V = \frac{|O_V|}{|T|} = \frac{|O_V^{(a)}| + |O_V^{(v)}|}{|T^{(a)}| + |T^{(v)}|} = (1 - \rho^{(v)})\frac{|O_V^{(a)}|}{|T^{(a)}|} + \rho^{(v)}\frac{|O_V^{(v)}|}{T^{(v)}}$$

Since $S^{(a)} = |O_V^{(a)}|/|T^{(a)}|$ is the arterial saturation, and $S^{(v)} = |O_V^{(v)}|/|T^{(v)}|$ is the venous saturation, $S_V$ can be expressed as:

$S_V = (1 - \rho^{(v)})S^{(a)} + \rho^{(v)}S^{(v)}$

If $|T(a)|=|T(v)|$, hence $\rho^{(v)}=1/2$, the resulting volume oscillating saturation, $S_V$ is a simple average between the arterial and venous saturation. If, however, the venous hemoglobin oscillations are greater than the arterial hemoglobin oscillations, such that $\rho^{(v)}>1/2$, $S_V$ will be skewed towards the venous saturation. In the case of spiroximetry, where it is assumed that $\rho^{(v)}\sim 1$, $S_V$ is an accurate measure of the venous saturation, $S^{(v)}$.

2 Alternatives

In certain examples described above, the hemoglobin saturation, $S_V$ is determined based on an assumed or inferred phase angle between $O_F$ and $O$ (i.e., $\text{Arg}(O_F)-\text{Arg}(O)$). However, in other examples, the value of the hemoglobin saturation of the time-varying vascular compartment, $S_V$ is assumed or inferred using the hemodynamic model and other quantities are determined based on that assumption.

Figure 12:
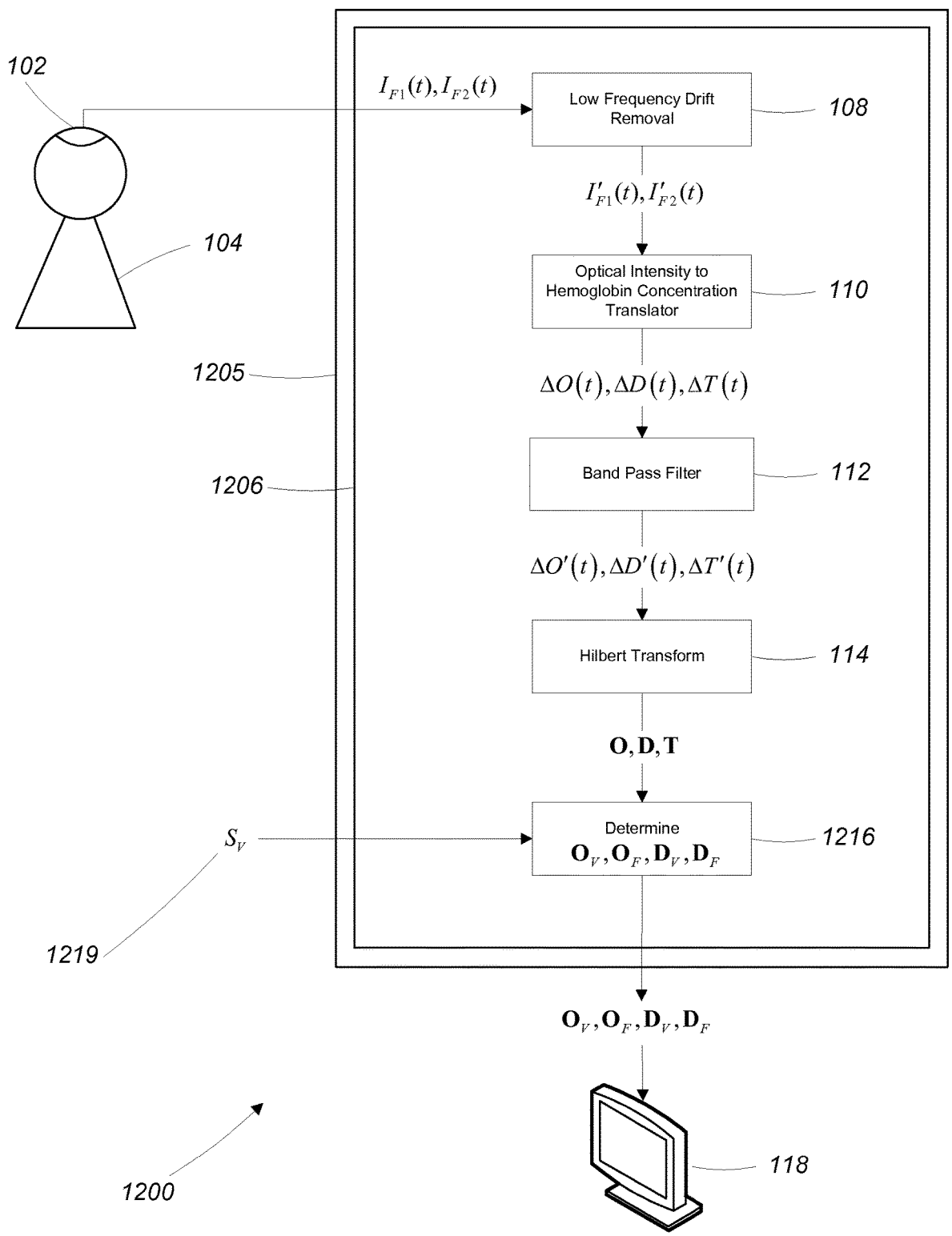
FIG. 12 is a schematic diagram of an oximetry system for determining volume and flow contributions to an oscillatory hemoglobin concentration.

For example, referring to FIG. 12, an optical oximetry measurement system 1200 includes an optical probe 102 secured to a body part of a subject 104, an oximetry processing module 1206 implemented on a computing device 1205, and a display device 118 (e.g., an LCD monitor). The oximetry processing module 1206 includes a low frequency drift removal module 108, optical intensity to hemoglobin concentration translator module 110, a band pass filter module 112, a Hilbert transform module 114, and a hemodynamic model based calculation module 1216.

The oximetry processing module 1206 operates in much the same way as the oximetry processing module 106 of FIG. 1 but instead of determining the hemoglobin saturation, $S_V$, the hemodynamic model based calculation module 1216 of the oximetry processing module 1206 determines the $O_V$, $O_F$, $D_V$, and $D_F$ phasors (using the techniques described above) based on an assumed or inferred hemoglobin saturation of the volume oscillating vascular compartment, $S_V$. For example, $O_V$ and $D_V$ are drawn along the direction of T, as given by $O_V=S_V T$ and $D_V=(1-S_V)T$. Then, since $O=O_V+O_F$ and $D=D_V+D_F$, $O_F$ and $D_F$ can be drawn as the phasors from the tip of $O_V$ to the tip of O and from the tip of $D_V$ to the tip of D, respectively.

In some examples, blood pressure measurements (i.e., mean arterial pressure or 'MAP' measurements) are used to obtain an estimate of an arterial component of oscillations in blood volume. The venous component of the oscillations in blood volume can then be determined based on the estimate of the arterial component of the oscillations.

3 Implementations

Systems that implement the techniques described above can be implemented in software, in firmware, in digital electronic circuitry, or in computer hardware, or in combinations of them. The system can include a computer program product tangibly embodied in a machine-readable storage device for execution by a programmable processor, and method steps can be performed by a programmable processor executing a program of instructions to perform functions by operating on input data and generating output. The system can be implemented in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

It is to be understood that the foregoing description is intended to illustrate and not to limit the scope of the invention, which is defined by the scope of the appended claims. Other embodiments are within the scope of the following claims.

What is claimed is:

1. A method for using a computer-implemented computational model to determine a hemoglobin saturation of a volume-oscillating vascular compartment in tissue with a non-negligible oscillating rate of supply of oxygenated blood to a portion of the tissue, the method including
    receiving data representing measurements of a plurality of oscillating hemoglobin concentrations from the tissue;
    receiving a representation of a phase offset between an oscillating oxygenated hemoglobin concentration measurement and an oscillating deoxygenated hemoglobin concentration measurement caused by an oscillating rate of supply of blood to the portion of the tissue, wherein the representation of the phase offset is either empirically derived or inferred using a coherent hemodynamics spectroscopy model; and
    using the representation of the phase offset to determine the hemoglobin saturation of the volume-oscillating vascular compartment to exclude an effect on the determined hemoglobin saturation of an oscillating rate of supply of oxygenated blood to the portion of the tissue by removing a contribution of the oscillating rate of supply of blood from the oscillating oxygenated hemoglobin concentration measurement, and
    providing the determined hemoglobin saturation for use in a medical setting;
    wherein the computer implemented computational model relates the effect of the oscillating rate of supply of oxygenated blood to the portion of the tissue to an oscillation in the measured concentration of oxygenated hemoglobin and an oscillation in the measured concentration of deoxygenated hemoglobin due to oscillations in blood flow to the portion of the tissue.

2. The method of claim 1 wherein the plurality of oscillating hemoglobin concentrations from the tissue include a measured concentration of oxygenated hemoglobin, a measured concentration of deoxygenated hemoglobin, and a total hemoglobin concentration.

3. The method of claim 1 wherein the plurality of oscillating hemoglobin concentrations oscillate at a frequency associated with a physiological function.

4. The method of claim 3 wherein the plurality of oscillating hemoglobin concentrations oscillate at a cardiac frequency.

5. The method of claim 3 wherein the plurality of oscillating hemoglobin concentrations oscillate at a respiratory frequency.

6. The method of claim 1 wherein the plurality of oscillating hemoglobin concentrations oscillate at a physically induced frequency.

7. The method of claim 1 wherein the oscillation in the measured concentration of oxygenated hemoglobin and the oscillation in the measured concentration of deoxygenated hemoglobin are at least in part due to diffusion of oxygen from blood to the portion of the tissue.

8. The method of claim 1 wherein the portion of the tissue includes a capillary compartment of the tissue.

9. The method of claim 1 wherein the volume-oscillating vascular compartment includes an arterial compartment.

10. The method of claim 1 wherein the volume-oscillating vascular compartment includes a venous compartment.

11. The method of claim 1 wherein the volume-oscillating vascular compartment includes a mixture of an arterial compartment and a venous compartment.

12. The method of claim 11 further comprising determining a first fraction of the hemoglobin saturation associated with the venous compartment and a second fraction of the hemoglobin saturation associated with the arterial compartment.

13. The method of claim 12 wherein the second fraction of the hemoglobin saturation is determined based on a blood pressure measurement.

14. The method of claim 12 wherein the first fraction and the second fraction are determined based on an empirically determined ratio.

15. The method of claim 1 wherein the hemoglobin saturation of the volume-oscillating vascular compartment is determined at least in part using a multi-compartment hemodynamic model.

16. A system for determining a hemoglobin saturation of a volume-oscillating vascular compartment in tissue with a non-negligible oscillating rate of supply of oxygenated blood to a portion of the tissue, the system including
a first input for receiving data representing measurements of a plurality of oscillating hemoglobin concentrations from the tissue;
a second input for receiving a representation of a phase offset between an oscillating oxygenated hemoglobin concentration measurement and an oscillating deoxygenated hemoglobin concentration measurement caused by an oscillating rate of supply of blood to the portion of the tissue, wherein the representation of the phase offset is either empirically derived or inferred using a coherent hemodynamics spectroscopy model; and
an oximetry processing module including a computer implemented computational model for using the representation of the phase offset to determine the hemoglobin saturation of the volume-oscillating vascular compartment to exclude an effect on the determined hemoglobin saturation of an oscillating rate of supply of oxygenated blood to the portion of the tissue by removing a contribution of the oscillating rate of supply of blood from the oscillating oxygenated hemoglobin concentration measurement; and
an output for providing the determined hemoglobin saturation for use in a medical setting;
wherein the computer implemented computational model relates the effect of the oscillating rate of supply of oxygenated blood to the portion of the tissue to an oscillation in the measured concentration of oxygenated hemoglobin and an oscillation in the measured concentration of deoxygenated hemoglobin due to oscillations in blood flow to the portion of the tissue.

17. The system of claim 16 further comprising a sensor for obtaining the data representing measurements of the plurality of hemoglobin concentrations from the tissue and providing the data to the first input.

18. The system of claim 16 further comprising a display device for receiving a representation of the determined hemoglobin saturation of the volume-oscillating vascular compartment from the output and presenting the representation of the determined hemoglobin saturation of the volume-oscillating vascular compartment.

19. The system of claim 16 wherein the oximetry processing module determines the hemoglobin saturation of the volume-oscillating vascular compartment is determined at least in part using a multi-compartment hemodynamic model.

* * * * *